United States Patent [19]

Weinblatt

[11] Patent Number: 4,483,681
[45] Date of Patent: Nov. 20, 1984

[54] METHOD AND APPARATUS FOR DETERMINING VIEWER RESPONSE TO VISUAL STIMULI

[76] Inventor: Lee S. Weinblatt, 797 Winthrop Ave., Teaneck, N.J. 07666

[21] Appl. No.: 464,760

[22] Filed: Feb. 7, 1983

[51] Int. Cl.³ .............................................. G09B 5/02
[52] U.S. Cl. ................................................... 434/236
[58] Field of Search .................. 434/236, 350; 352/39; 353/121; 346/419

[56] References Cited

U.S. PATENT DOCUMENTS

| | | | |
|---|---|---|---|
| 3,328,803 | 6/1967 | Schwerin | 434/350 X |
| 3,388,630 | 6/1968 | Leitner | 434/236 |
| 3,622,236 | 11/1971 | Novy | 353/86 |
| 4,075,657 | 2/1978 | Weinblatt | 358/93 |
| 4,097,134 | 6/1978 | Jerie | 353/86 X |
| 4,231,643 | 11/1980 | Demick et al. | 353/86 |

Primary Examiner—William H. Grieb
Attorney, Agent, or Firm—Natter & Natter

[57] ABSTRACT

A system for monitoring viewer response to visual stimuli having two slide projectors keyed for the simultaneous slide transport and optional viewing modes. The procedure includes projecting images from one slide projector, as seen at a normal viewing distance and providing viewer control for selectively switching to the other slide projector for projecting an enlarged close-up view of the same image. A recording apparatus is included for denoting the subject matter viewed in the enlarged format.

10 Claims, 3 Drawing Figures

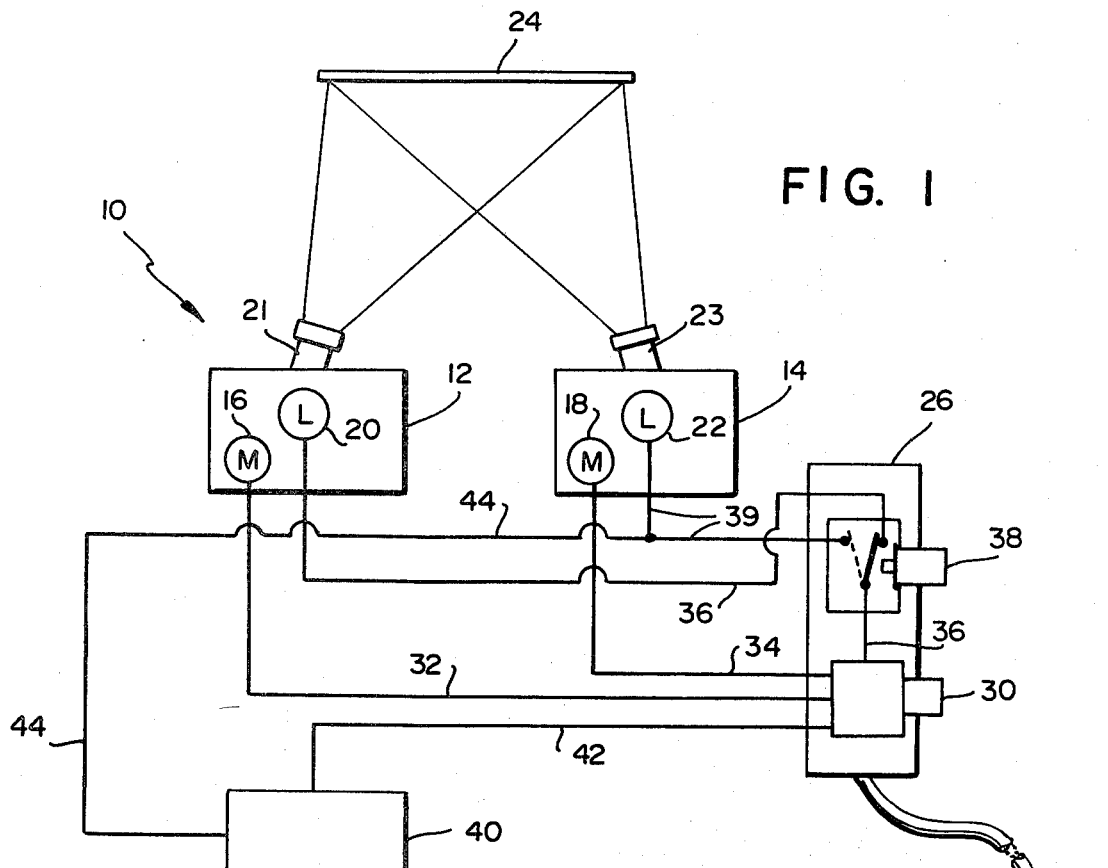
FIG. 1
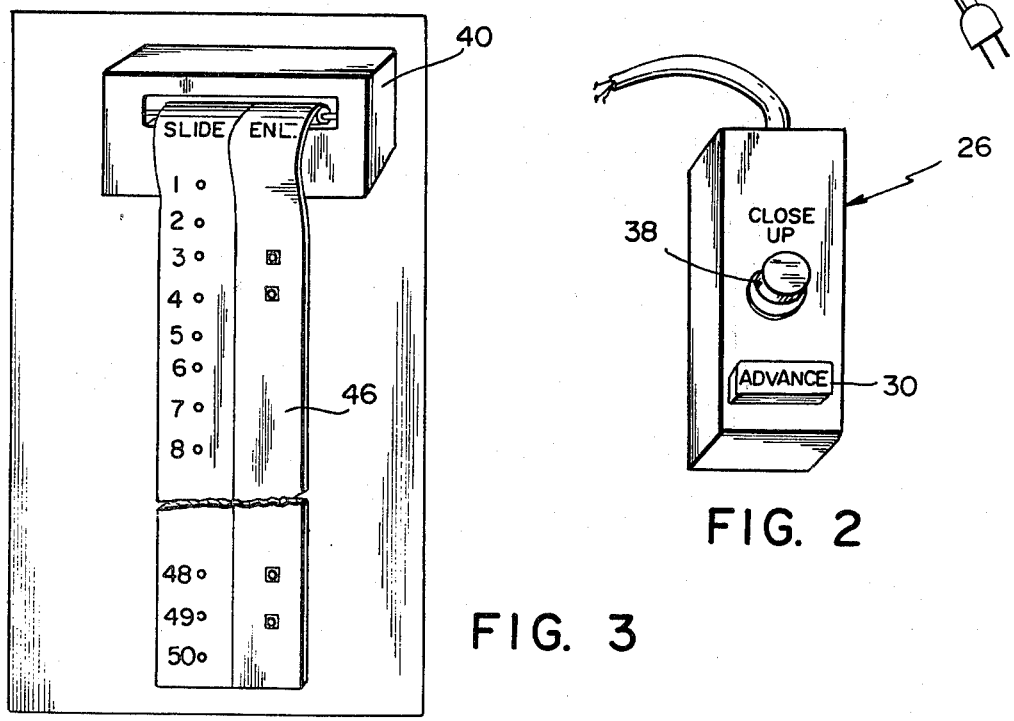
FIG. 2
FIG. 3

METHOD AND APPARATUS FOR DETERMINING VIEWER RESPONSE TO VISUAL STIMULI

TECHNICAL FIELD

This invention concerns media survey techniques and especially a system for measuring response to stimuli and for denoting visual materials that are particularly effective in creating a viewer impact.

In particular, this invention involves an imaging system providing alternate viewing modes which can be monitored by a test subject with selective control of the viewing mode.

BACKGROUND ART

Various consumer survey procedures have been utilized for measuring consumer response to advertising materials and product packaging. One method directed to on-shelf packaging performance was to use an eye movement recorder. That system included photographically reproducing a simulated scene presented as if a test subject was walking through a supermarket or similar environment. An eye movement recorder was then used to observe if the test subject's eye was fixed on any of the products shown on a projection screen. A typical example of such an eye movement monitoring apparatus as shown in U.S. Pat. No. 4,075,657. A problem of that testing procedure was that it only indicated if the test subject noticed the product, but it was not an indicator as to whether it successfully aroused or provoked further action.

Another shortcoming with that type of eye motion study was that it did not duplicate actual conditions of a representative purchaser. In particular, a consumer after noticing a package may have expressed further interest and a desire to more carefully examine the product, read the label, check the ingredients, etc. This reaction could not be detected with the aforementioned photographic surveying procedure, since the products typically appeared approximately five feet from the camera which was intended to simulate the location of a consumer walking down the middle of a shopping aisle. Although a purchaser may have been initially attracted to a package and this fact was observed using the eye movement detection procedure, there was still a possibility that the consumer would continue moving down the aisle without purchasing the product; however once the consumer inspects the package there is a greater likelihood of actual purchase. Thus, with the prior test method it was not possible to fully assess consumer interest and concomitant package performance.

The tandem imaging system of this invention is an improvement over the pior art in that it has the capability of delivering enlarged viewing images, on demand, through a multiple projection arrangement. Conventional plural display projection equipment such as those described in U.S. Pat. Nos. 3,622,236 and 4,231,643 utilized a dissolve mechanism for alternately phasing each projector in sequence to present successive displays in a continuous slide show on a single screen. Those prior art devices, however, were not coordinated for responding to viewer command or keyed for selective presentation of detailed views. It should, therefore, be apparent that a market survey procedure that could measure consumer reaction as induced by visual stimuli would provide a more accurate indication of the impact created upon the viewer.

SUMMARY OF THE INVENTION

Briefly, the nature of this invention concerns a system for monitoring view response to visual stimuli including a pair of slide projectors each having corresponding slide images and being interfaced for simultaneous slide transport so as to selectively project optional viewing modes of the same image.

The procedure includes projecting images onto a single screen from one projector which typically shows the subject matter as photographed at a camera range representing normal viewing distance and providing viewer controls for switching to a second projector for displaying a corresponding slide image in an alternate "close-up" mode. A recording and printing device can be utilized for indicating when these changes in viewing modes occur and for registering the respective image subject matter that evoked these responses.

It should thus be observed that the method and apparatus of this invention provides a comprehensive market research tool and a more accurate indication of product impact.

In view of the foregoing, it should be apparent that the present invention overcomes many of the shortcomings of the prior art and provides an improved method and apparatus for determining visual impact as a measure of package performance.

Having thus summarized the invention, it will be seen that it is an object thereof to provide a method and apparatus for determining the effectiveness of advertising materials and product packaging of the general character described herein which is not subject to the aforementioned disadvantages.

Specifically, it is an object of this invention to provide a method and apparatus for evaluating consumer response to selected stimuli.

Another object of this invention is to provide a method for measuring visual impact using a dual projection system with on-demand close-up viewing capabilities.

A still further object of this invention is to provide a method and apparatus for registering consumer interest which is simple in construction, low in cost and readily adapted for practical applications.

With these ends in view, the invention finds embodiment in certain combinations of elements and arrangements of parts by which the objects aforementioned and certain other objects are hereinafter attained, all as more fully described with reference to the accompanying drawings and the scope of which is more partucularly pointed out and indicated in the appended claims.

BRIEF DESCRIPTION OF THE DRAWINGS

In the accompanying drawings in which is shown a possible exemplary embodiment of the invention:

FIG. 1 is a schematic representation illustrating the apparatus of this invention and showing two slide projectors, a viewing screen, a remote projection selector control and a printer;

FIG. 2 is an isolated perspective view showing the projection selector for "advance" and "close-up" viewing; and FIG. 3 is a typical data printout from the recorder printer showing a recorder of close-up viewing keyed to the corresponding slide image.

BEST MODE FOR CARRYING OUT THE INVENTION

Referring now in detail to the drawings, the reference numeral 10 denotes generally the apparatus of this invention for determining viewer response to visual stimuli. The apparatus 10 as illustrated in FIG. 1 includes a pair of slide projectors 12, 14 each of which includes a slide transport mechanism (not shown), a motor 16, 18 for operating the respective slide transport mechanisms and a projection lamp 20, 22 for illuminating a slide and projecting the image through a lens system 21, 23 on a viewing screen 24. By way of example, a typical slide projector suitable for this arrangement is the Carousel slide projector manufactured by the Eastman Kodak Company, e.g. Model 4400 or 5200. The projectors 12, 14, as noted, are positioned for focussing the respective projected images upon the viewing screen 24. In addition, a projection selector control 26 is utilized for operating the projectors 12, 14.

Referring now to FIG. 2, it should be noted that a conventional AC power source is fed to the control 26, and when a slide "advance" switch 30 is activated the motor 16, 18 will be energized through circuits 32, 34 for simultaneously operating the motors 16, 18 and corresponding slide transport mechanisms.

It should be further noted that the "advance" switch 30 will also provide power through circuit 36 for illuminating the projection lamp 20. Although the activation of advance switch 30 will operate the slide mechanisms of both projectors 12 and 14, the slide images will only be projected on screen 24 from projector 12 since only the lamp 20 has been energized. In order to project the slide images of slide projector 14, a close-up switch 38 has been provided which is a double-pole, double throw or equivalent type switch such that the operation of the switch 38 will provide current through a line 39 to illuminate lamp 22 and at the same time open circuit 36.

In accordance with the method of this invention, each of the slide projectors 12, 14 are coordinated such that the slides within projector 12 show the viewing material at a normal range whereas corresponding slides within projector 14 contain matching images enlarged for close-up viewing. The slides are loaded in the respective slide mechanisms so that by operation of the close-up switch 36 a magnified view of the subject matter in projector 14 will automatically appear on the screen 24. Since the operation of the control 26 is under the command of the test subject, the number of times the close-up switch 38 is utilized and the enlarged image slides are viewed provide a data base for market research.

Although this information can be collected by observation of the test subject and manual record keeping, an electromechanical or digital printer can be integrated into the system. A printing device 40 can be interfaced and activated by the advance switch 30 with a circuit 42 providing a pulse corresponding to the slide advancement and a circuit 44 being in communication with circuit 39 can be used to signal whenever the close-up switch 38 is applied. It should be noted that in the foregoing description and corresponding drawing the neutral leg of the circuits has been omitted for clarity.

A printout 46 is typically shown in FIG. 3 which provides a record of the test subject's responses to each of these slides as projected and can serve as a permanent record for later use.

It should further be understood that in place of using two photographic slide sets with matched images in each of the two projectors, an alternate mode of operation can include a single projector having alternating close-up and normal view images wherein the slide transport is sequenced for showing every "second" slide image. When the viewer wishes to more closely examine the projected material, the transport mechanism can then be advanced to the next immediate slide being in the enlarged view rather than every other slide showing normal observation range.

It should thus be seen that the plural projection apparatus of this invention provides an improved and efficient method for determining visual impact as a measure of performance and is well adapted to meet conditions of practical usage.

Furthermore, this procedure can be used for other than surveying package performance, e.g. in market testing advertising materials for a mailing campaign to determine whether the recipient will be interested enough to open the envelope based upon the printed content on the outside of the envelope.

Since various possible embodiments may be made of the invention and further changes may be incorporated in the exemplary embodiment and methods set forth herein, it is to be understood that all materials set forth and shown in the accompanying drawings are to be interpreted as illustrative and not in a limiting sense.

Having thus described the invention, there is claimed as new and desired to be secured by Letters Patent:

1. A method for determining viewer response to visual stimuli comprising the steps of
   (a) presenting programmed visual stimuli in a viewing mode having a sequential display of images for simulating a realistic environment as experienced by the viewer including a corresponding display of images in an alternate viewing mode,
   (b) providing viewer selection control for activating the alternate viewing mode, and
   (c) registering selection control of the alternate viewing mode as a measure of viewer response to the visual stimuli.

2. A method for determining viewer response to visual stimuli as claimed in claim 1 wherein the stimuli are presented using plural image display systems, said display systems being simultaneously operable and selectively viewable.

3. A method for determining viewer response to visual stimuli as claimed in claim 2 wherein the image display systems include dual slide projectors with each slide projector having corresponding slide images with said slide projectors being interfaced for simultaneous slide transport.

4. A method for determining viewer response to visual stimuli as claimed in claim 3 wherein one of said slide projectors is adapted for projecting images as viewed from a predetermined camera range and the other of said slide projectors is adapted for projecting corresponding images as viewed from an alternate camera range.

5. A method for determining viewer response to visual stimuli as claimed in claim 4 wherein each of said slide projectors is provided with illumination means for projecting slide images, said illumination means being independently activated and responsive to the selected viewing mode.

6. A method for determining viewer response to visual stimuli as claimed in claim 5 further including printing means for recording viewer selection of the alternate viewing mode.

7. An apparatus for determining viewer response to visual stimuli comprising a plural image display system having first projection means for displaying a series of projected images, second projection means keyed to the first projection means for displaying a series of related alternate images, and viewer command means for selectively activating said second projection means to display the related alternate images.

8. An apparatus for determining viewer response to visual stimuli including a pair of slide projectors, plurality of photographic slide sets, the slides in each set presenting matched images, said projectors being interfaced for simultaneously registering the matched images of each set for projection, control means for selectively projecting the slide images of either of said slide projectors.

9. An apparatus for determining viewer response to visual stimuli as claimed in claim 8 wherein the slides in one of said projectors are programmed for projectinng images as viewed at a normal observation range, and the slides of the other projector being adapted for projecting enlarged images as viewed at a closeup range.

10. An apparatus for determining viewer response to visual stimuli as claimed in claim 9 further including recording means for indicating when the enlarged images are viewed.

* * * * *